US007798942B2

(12) United States Patent
Digiulio et al.

(10) Patent No.: US 7,798,942 B2
(45) Date of Patent: Sep. 21, 2010

(54) AUTOMATED PERSONAL TRAINER

(76) Inventors: David M. Digiulio, 1322 Schodack Valley Rd., Castleton, NY (US) 12033; Kevin C. Craig, 31 Glenmore Ave., Saratoga Springs, NY (US) 12866; Matthew Rosmarin, 157-23 26th Ave., Flushing, NY (US) 11354

(*) Notice: Subject to any disclaimer, the term of this patent is extended or adjusted under 35 U.S.C. 154(b) by 551 days.

(21) Appl. No.: 11/463,416

(22) Filed: Aug. 9, 2006

(65) Prior Publication Data
US 2007/0038473 A1    Feb. 15, 2007

Related U.S. Application Data

(60) Provisional application No. 60/706,612, filed on Aug. 9, 2005.

(51) Int. Cl.
*A63B 71/00* (2006.01)
(52) U.S. Cl. ............................... 482/8; 482/1
(58) Field of Classification Search ............ 482/8, 482/91, 1
See application file for complete search history.

(56) References Cited

U.S. PATENT DOCUMENTS 4,779,865 A * 10/1988 Lieberman et al. ............ 482/8
5,435,798 A * 7/1995 Habing et al. .................. 482/5
6,053,845 A * 4/2000 Publicover et al. ............ 482/35
7,063,644 B2   6/2006 Albert et al.
2005/0020415 A1* 1/2005 Reno ........................... 482/91
2005/0270280 A1* 12/2005 Riback et al. ................ 345/204
2005/0272561 A1* 12/2005 Cammerata .................... 482/8
2006/0100074 A1* 5/2006 Murdoch .................... 482/142
2006/0229164 A1* 10/2006 Einav ............................ 482/9
2006/0237604 A1* 10/2006 Tan .......................... 248/205.3
2006/0293151 A1* 12/2006 Rast .............................. 482/8

* cited by examiner

*Primary Examiner*—Loan Thanh
*Assistant Examiner*—Shila Abyaneh
(74) *Attorney, Agent, or Firm*—Jayme M. Torelli; Hoffman Warnick LLC

(57) ABSTRACT

The present invention allows users to monitor their workouts using a small, portable device which provides feedback regarding speed of exercise repetition and range of motion, enabling the user to use pneumatic or cable driven workout structures safely, efficiently, and effectively. In a typical embodiment, the present invention allows a user to define pre-set requirements, attach the device to a cable-driven exercise structure, and complete the exercise while using the device to monitor the exercise. The device signals to the user if the user's execution of exercise repetitions falls outside the user's pre-set requirements for speed and range of motion. The results of the user's exercise repetitions are displayed on a display screen and are stored in the device's memory, and may then be uploaded onto the user's personal computer to further monitor progress.

20 Claims, 7 Drawing Sheets

AUTOMATED PERSONAL TRAINER

CROSS-REFERENCE TO RELATED APPLICATION

The current application claims the benefit of U.S. Provisional Application No. 60/706,612, filed on Aug. 9, 2005, which is hereby incorporated herein by reference.

BACKGROUND OF THE INVENTION

1. Field of the Invention

The present invention relates generally to an automated feedback and monitoring device that provides feedback to users during their exercise routines, enabling them to work out safely, efficiently, and effectively, without the expense of a personal trainer. The device is portable, easy to install on any cable-driven workout structure, and measures range of motion, speed of an exercise repetition, and weight used over a set of repetitions, stores the results electronically, and provides access to an internet application for reporting exercise results and an online community offering support, exercise tips, and nutritional guidelines.

2. Related Art

Membership retention is an ongoing problem for fitness centers. Although there are a variety of reasons for membership attrition, lack of motivation and visual progress are major reasons for drops in membership. To combat member attrition rates at fitness centers, a number of products are currently available.

ActivTrax® provides a web-based application interface that creates customized and evolving exercise routines based on data input by the user. To begin using the program, a user inputs various data pertaining to the user's physical fitness level, physical size, gender, etc., and equipment available to the user, and ActivTrax® professionals generate a suitable workout for the user. To generate subsequent workouts, the user logs into the website after finishing a workout and inputs data pertaining to the user's results during the previously generated workout. ActivTrax® then generates a subsequent workout based in part on results from the first workout that follows the first in an evolving progression. While ActivTrax® generates appropriate workouts, it fails to include any features that offer support during workouts, real time feedback and user monitoring during exercising, or feedback regarding completed workouts.

FitLinxx® provides a computerized system that is hardwired directly into existing fitness equipment. Users' individual workout programs are pre-programmed into the FitLinxx® system, and the system tracks the user's progress from workout to workout and monitors the user's form during exercises. To facilitate tracking and monitoring, the user must memorize an access code, and enter it each time he or she uses a piece of equipment. A personal trainer predetermines the appropriate amount of weight, number of repetitions, and speed of the repetitions for each workout. At the end of the set on each machine, the FitLinxx® system prompts the user to see if they would like to increase the amount of weight for the next set. This restricts users from modifying the routine in real time. FitLinxx® also requires that each separate piece of equipment that an individual uses have an computerized system installed on it. The device is not portable, nor does it allow the user any control over his or her own workout.

Today's healthcare industry also has need for a system for monitoring patients receiving physical therapy. Healthcare providers must prepare a tremendous amount of documentation in order to receive payment for services rendered. In addition, third party payors negotiate capitated rates (maximum reimbursement level) that participating providers have to bill for particular services. The combination of increased documentation requirements and capitated payments makes profitability of physical therapy services difficult. There is a need in the art for an automated device which provides the necessary data collection and storage for documentation for use in the healthcare industry.

As can be seen, current computerized personal trainer-replacement technologies provide only rigid, pre-programmed workouts for users, and fail to provide detailed documentation of exercise results. No existing system has developed a way whereby a portable, easy-to-install device monitors weight, range of motion, speed of exercise repetition, and provides the necessary feedback during the course of the workout to maintain a safe workout environment in the absence of one-on-one attention from a personal trainer. In view of the foregoing, there exists a need in the art to overcome one or more of the deficiencies indicated herein.

SUMMARY OF THE INVENTION

The present invention is a feedback and monitoring device that provides feedback to users during their exercise routines, allowing them to workout safely, effectively, and efficiently, without the expense of a personal trainer or physical therapist. The small, portable Automated Personal Trainer (APT) device measures and monitors speed of exercise repetition(s), range of motion of exercise repetition(s), and weight used, and stores, displays, and allows for uploading of results to an Internet application. The invention also provides for access to an online community offering exercise tips, nutritional guidelines, and online support.

According to a first aspect of the invention, a method for monitoring and guiding a user through an exercise program, comprising: providing a portable monitoring device on a workout structure for monitoring at least one exercise repetition; determining a result of the at least one exercise repetition, including a speed by which the user is performing the at least one exercise repetition and a range of motion by which the user is performing the at least one exercise repetition; and storing the result in a portable memory device for upload to a personal computer for monitoring and guiding the user through the exercise program.

According to a second aspect of the invention, a system for monitoring and guiding a user through an exercise program, comprising: a system for determining a result of an exercise repetition, the result including a speed by which the user is performing the exercise repetition and a range of motion by which the user is performing the exercise repetition; a system for storing the result or a plurality of results in a portable memory device; and a system for uploading the result or the plurality of results in the portable memory device to a personal computer for monitoring and guiding the user through the exercise program.

According to a third aspect of the invention, a program product stored on a computer readable medium is provided for monitoring and guiding a user through an exercise program. The computer readable medium comprises program code for causing a computer system to perform the following steps: determining a result of at least one exercise repetition by using a portable monitoring device attached to a workout structure, the result including a speed by which the user is performing the at least one exercise repetition and a range of motion by which the user is performing the at least one exercise repetition, and displaying the result to the user; providing a signal to the user, based on the result, if the speed and the range of motion fail to meet a predetermined requirement; storing the result in a portable memory device; and uploading the result in the portable memory device to a personal computer for monitoring and guiding the user through the exercise program.

According to a fourth aspect of the invention, a device is provided for monitoring and displaying the results of a user's exercise repetitions. The device comprises: a pulley unit for collecting exercise result data; a monitoring unit for displaying and storing the exercise result data; and a means for communicating the exercise result data from the pulley unit to the monitoring unit.

According to a fifth aspect of the invention, a software application is provided for importing exercise result data from an automated personal trainer device to allow for monitoring and review of a user's exercise history and performance and guiding the user through an exercise program.

According to a sixth aspect of the invention, a computer system is provided for determining, displaying, storing, and uploading exercise result data.

BRIEF DESCRIPTION OF THE DRAWINGS

These and other features of this invention will be more readily understood from the following detailed description of the various aspects of the invention taken in conjunction with the accompanying drawings in which.

Figure 1:
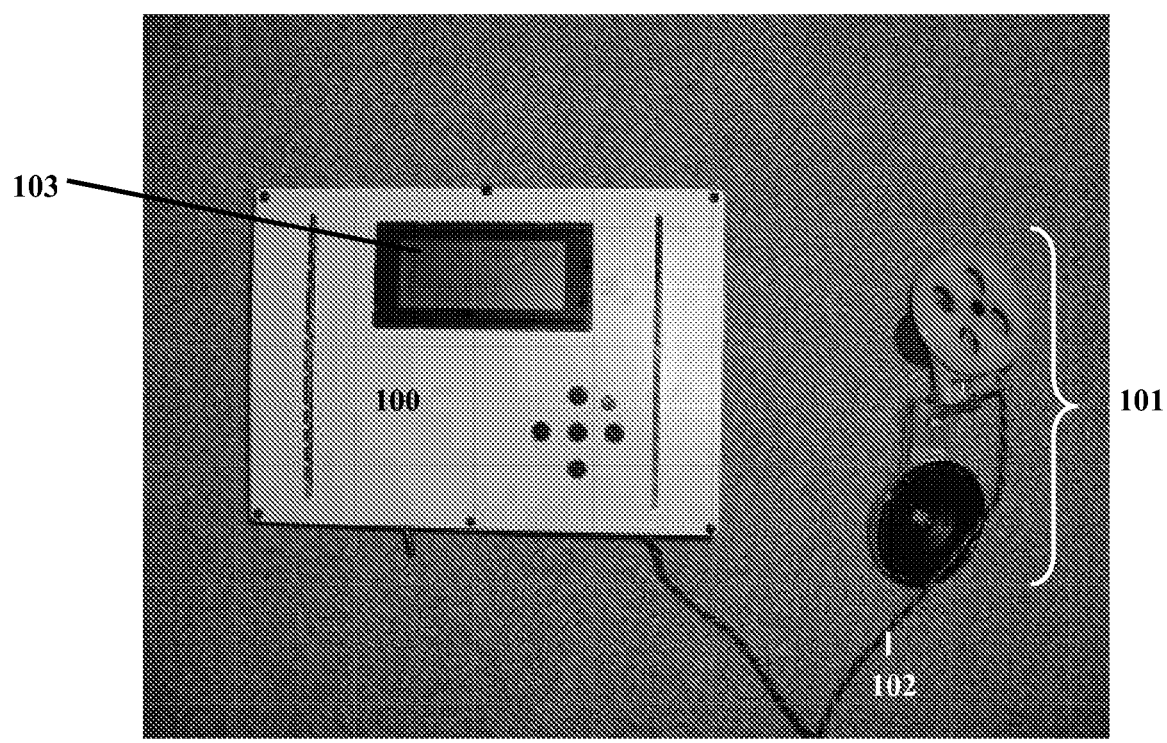
FIG. 1 depicts an Automated Personal Trainer (APT) device, including a monitoring unit and a pulley unit linked by wires.

It is noted that the drawings of the invention are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

Generally stated, the present invention provides a device, a method, and a system which provide a user with feedback during an exercise routine, enabling the user to workout safely, efficiently, and effectively without the expense of a personal trainer. The device, system, and method may be used with any existing exercise structure which is cable-driven, regardless of whether resistance is provided via hydraulic, pneumatic, or mass resistance. Specifically, a pulley unit collects data indicating the speed of the user's exercise repetition(s), the range of motion of the exercise repetition(s), and weight used. This information is relayed to a monitoring unit via a wire. The monitoring unit displays and stores the data on a memory stick, and allows for uploading of the results to an internet application. The invention also allows for the user to obtain access to an online internet community which features, inter alia, nutrition information, exercise tips, and online support.

Referring now to FIG. 1, an illustrative embodiment of the present invention will be described in further detail. As depicted, FIG. 1 illustrates monitoring unit 100 and pulley unit 101, linked by wire 102. Pulley unit 101 collects exercise repetition data throughout the course of a user's workout, and transmits the data through wire 102 to the monitoring unit 100. Monitoring unit 100, which is powered by a 9-volt rechargeable battery, stores data collected during each exercise on memory stick, and displays the results of the each exercise in real time on display screen 103.

The present invention collects data and monitors a user's exercise results through several parameters. A range of motion feature allows a user to define target extended and rescinded position values for each exercise. If the user exceeds either or both of these values, monitoring unit 100 signals in real time to the user. This feedback signal feature enables a user to optimize each repetition by attaining full safe range of motion in each direction during each repetition. A speed feature allows a user to set a second parameter by defining a target speed at which the user will move through the range of motion during each repetition. Specifically, the user inputs a desired number of seconds that it should take the user to move the weight (or resist hydraulic or pneumatic pressure) over the range of motion, to accommodate any of a variety of exercise techniques and strategies known in the art. The real time feedback display enables the user to maintain a constant, consistent, and maximally effective speed of motion. A weight feature allows a user to set a third parameter by defining a target weight for workout optimization.

After the completion of an exercise or exercises, a user may then export the saved exercise result data from monitoring unit 100's memory stick into a software application on a personal computer to monitor and review the user's performance history. This feature of the claimed invention provides users who do not workout with a personal trainer with the motivation and feedback to see positive results over time. For users who work with a therapist or trainer, this eliminates the need for a therapist or trainer to stand over the user and manually record repetitions to be included in case notes. This reduction in transaction time allows therapists to increase the number of patients they can oversee at a given time, ultimately increasing the profitability of a practice.

Figure 2:
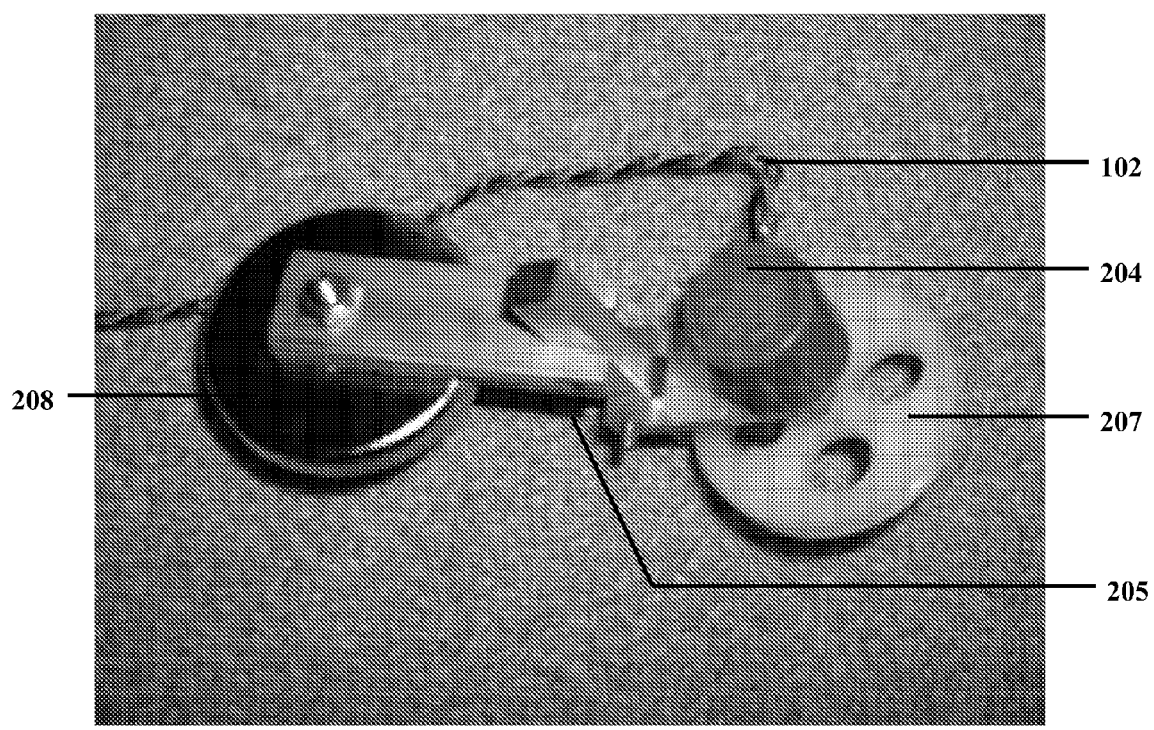
FIG. 2 depicts a posterior view of the pulley unit in detail.
Figure 3:
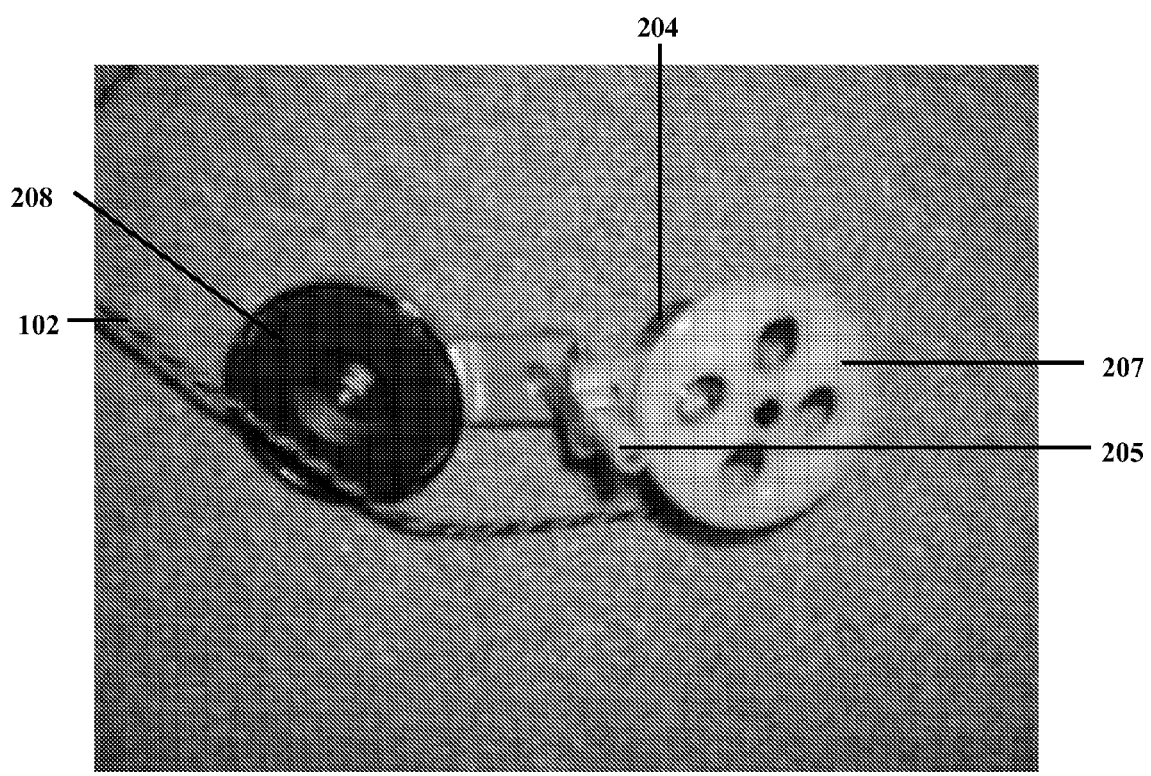
FIG. 3 depicts an anterior view of the pulley unit in detail.
Figure 4:
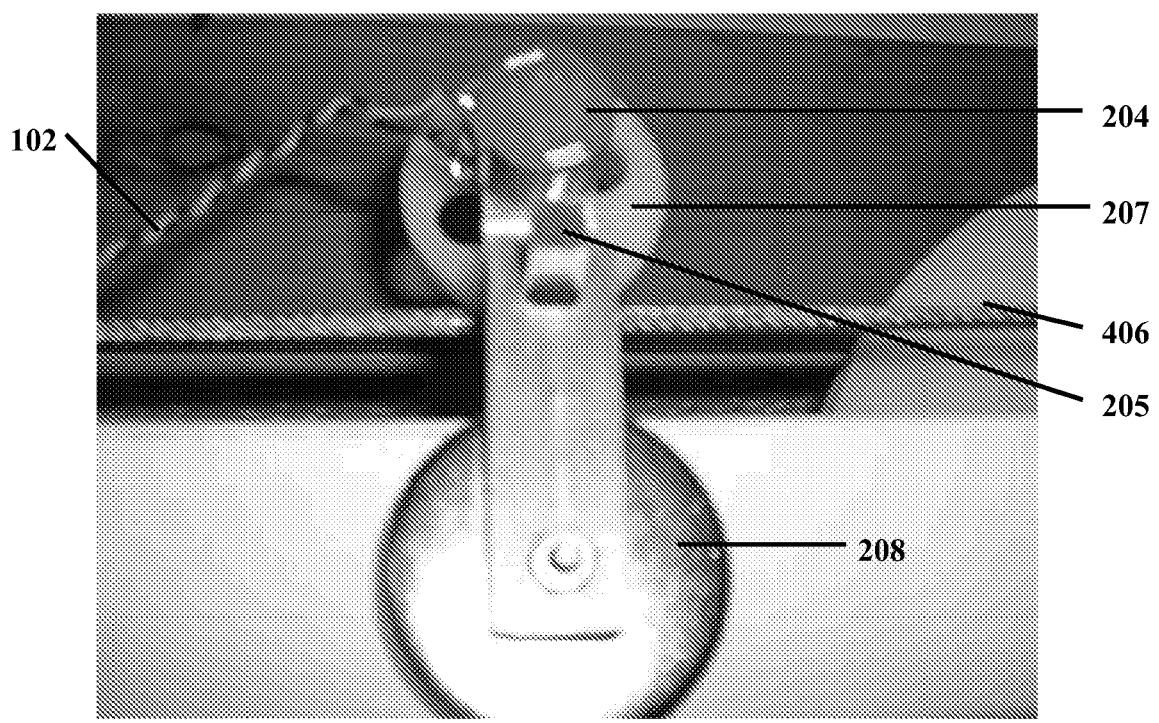
FIG. 4 depicts the pulley unit in use with a cable.

Referring now to FIGS. 2-4, these figures depict pulley unit 101 in detail. FIGS. 2 and 3 depict the pulley unit 101 by itself; while FIG. 4 depicts pulley unit 101 in use with guide wire 406. As shown in FIGS. 2 and 3, pulley wheels 207 and 208 are joined by spring-like metal clip 205. To attach pulley unit 101 to cable 406 of any cable-driven exercise structure, clip 205 attaches to cable 406, causing wheels 207 and 208 to pinch the cable with sufficient force to accurately maintain resistance data collection. With wheels 207 and 208 pinching the cable, the user executes the exercise. Potentiometer 204, attached to the axle of wheel 207, allows measurement of the movement of wheel 207 as the user completes the exercise. Data collected in this manner is then transmitted back to the monitoring unit 101 via wire 102, and displayed on display screen 103 and stored on a memory stick (not illustrated). FIG. 4 illustrates pulley unit 101 engaged with cable 406, which may be the cable of any cable-driven exercise equipment.

Figure 5:
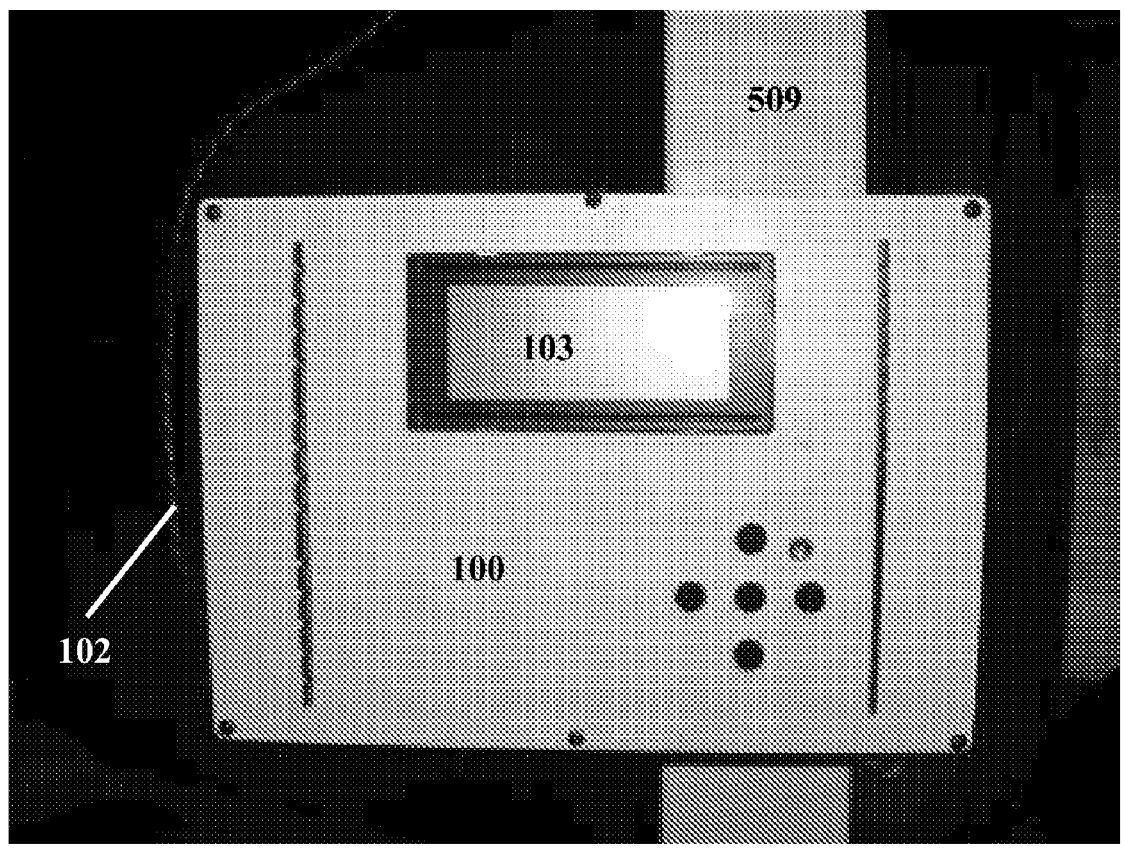
FIG. 5 depicts the APT device monitoring unit mounted to an existing exercise structure.
Figure 6:
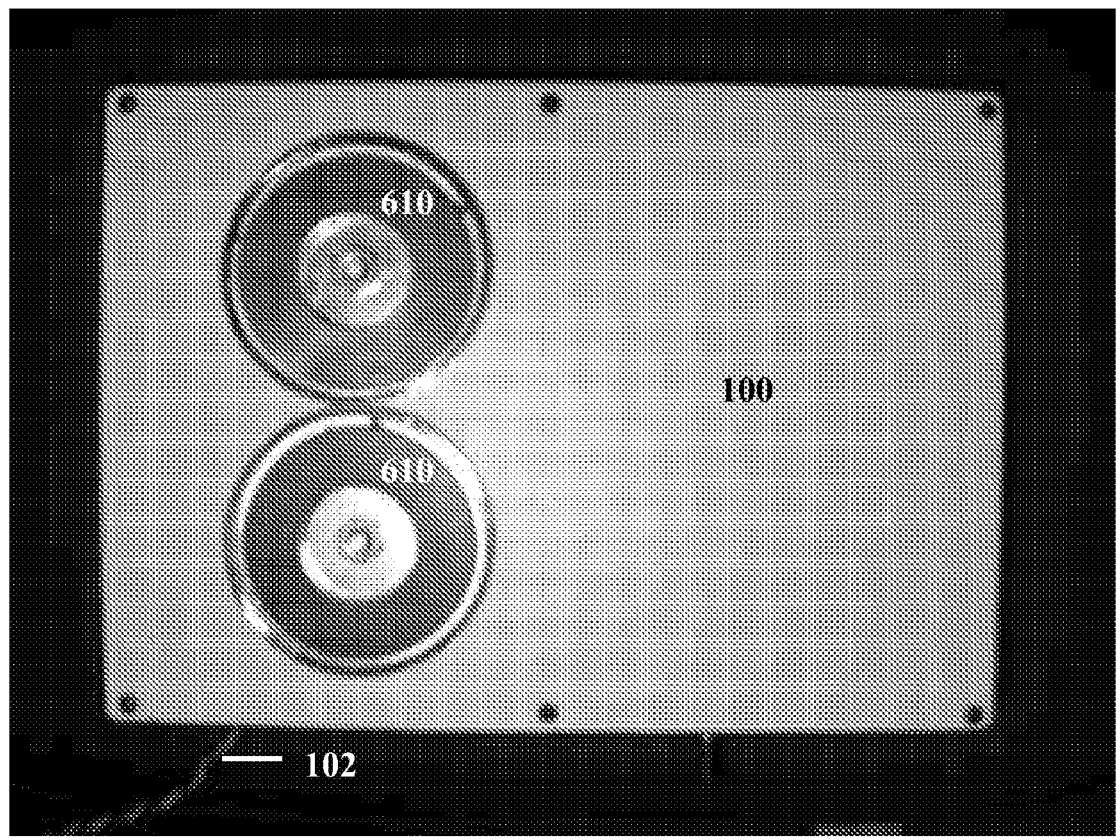
FIG. 6 depicts a posterior view of the APT monitoring unit including magnets.

Referring now to FIG. 5, this figure depicts APT device monitoring unit 100, which can be removably attached to any existing exercise structure 509. FIG. 6 depicts a posterior view of one possible embodiment of APT monitoring unit 100, including magnets 610, which allow the monitoring unit 100 to be temporarily affixed to an existing exercise structure 509, as shown in FIG. 5, and easily removed for use on a different existing exercise structure. Magnets 610 may be replaced by a clip or any other form of temporary, removable affixation known in the art.

Figure 7:
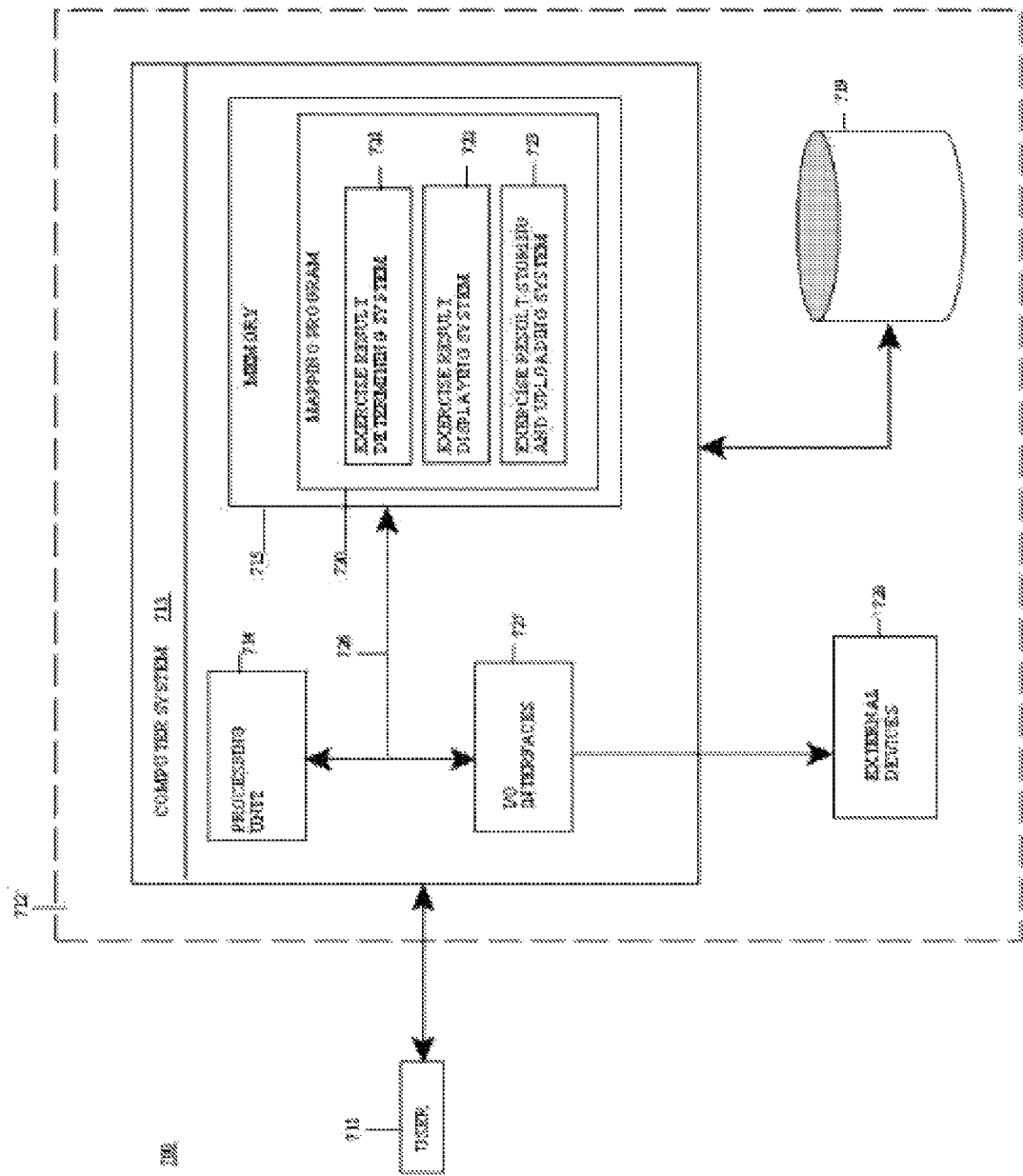
FIG. 7 depicts a computer system for determining, displaying, storing, and uploading exercise result data according to the present invention.

Referring now to FIG. 7, a diagram of a computerized implementation 700 of the present invention is shown. Implementation 700 includes APT monitoring unit 100 of FIGS. 1-6 (shown in FIG. 7 as computer system 713) deployed within a computer infrastructure 712. This is intended to demonstrate, among other things, that the present invention could be implemented within a network environment (e.g., the Internet, a wide area network (WAN), a local area network (LAN), a virtual private network (VPN), etc.), or on a stand-alone computer system. In the case of the former, communication throughout the network can occur via any combination of various types of communications links. For example, the communication links can comprise addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer infrastructure 712 is intended to demonstrate that some or all of the components of implementation 700 could be deployed, managed, serviced, etc. by a service provider who offers to generate source code for a function according to the present invention.

As shown, computer system 713 includes a processing unit 714, a memory 715, a bus 716, and input/output (I/O) interfaces 727. Further, computer system 713 is shown in communication with external I/O devices/resources 728 and storage system 719. In general, processing unit 714 executes computer program code, such as mapping program 720, which is stored in memory 715 and/or storage system 719. While executing computer program code, processing unit 714 can read and/or write data to/from memory 715, storage system 719, and/or I/O interfaces 727. Bus 716 provides a communication link between each of the components in computer system 713. External devices 728 can comprise any devices (e.g., keyboard, pointing device, display, etc.) that enable a user to interact with computer system 713 and/or any devices (e.g., network card, modem, etc.) that enable computer system 713 to communicate with one or more other computing devices.

Computer infrastructure 712 is only illustrative of various types of computer infrastructures for implementing the invention. For example, in one embodiment, computer infrastructure 712 comprises two or more computing devices (e.g., a server cluster) that communicate over a network to perform the various process steps of the invention. Moreover, computer system 713 is only representative of various possible computer systems that can include numerous combinations of hardware. To this extent, in other embodiments, computer system 713 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively. Moreover, processing unit 714 may comprise a single processing unit, or be distributed across one or more processing units in one or more locations, e.g., on a client and server. Similarly, memory 715 and/or storage system 719 can comprise any combination of various types of data storage and/or transmission media that reside at one or more physical locations. Further, I/O interfaces 727 can comprise any system for exchanging information with one or more external devices 728. Still further, it is understood that one or more additional components (e.g., system software, math co-processing unit, etc.) not shown in FIG. 7 can be included in computer system 713. However, if computer system 713 comprises a handheld device or the like, it is understood that one or more external devices 728 (e.g., a display) and/or storage system(s) 719 could be contained within computer system 713, not externally as shown.

Storage system 719 can be any type of system (e.g., a database) capable of providing storage for information under the present invention such as exercise result data, including weight, range of motion, and speed of repetition. To this extent, storage system 719 could include one or more storage devices, such as a magnetic disk drive or an optical disk drive. In another embodiment, storage system 719 includes data distributed across, for example, a local area network (LAN), wide area network (WAN) or a storage area network (SAN) (not shown). Although not shown, additional components, such as cache memory, communication systems, system software, etc., may be incorporated into computer system 713.

Shown in memory 715 of computer system 713 is mapping program 720, which includes exercise result determining system 721, and exercise result displaying system 722, and exercise result storing and uploading system 723. It should be understood that representation of mapping program 720 is intended only to illustrate one possible way of providing the functionality described herein. As such, the functionality described herein could be represented by a different configuration of systems (e.g., the functions provided by the systems of mapping program 720 could be combined into fewer systems or further separated into additional systems). In addition, although the functionality of the present invention is described herein as being carried out by a single program (e.g., mapping program 720), this need not be the case. For example, multiple different programs could be implemented to achieve the desired function (e.g., mapping program 720 could leverage existing technology in providing its desired results).

Regardless, exercise result determining system 721 will be leveraged by user 711 to provide collect result data during the user's execution of an exercise. Results from the potentiometer are delivered to exercise result determining system via wire 102, and according to the present invention. System 721 converts the data to a form, i.e. weight used, speed of repetition, and range of motion over which the exercise was executed, that is useful for guiding and monitoring a workout.

Once the results have been determined, exercise result displaying system 722 uses the same to generate a real time display indicating to user 711 the results of his or her workout in progress. System 722 further includes the capability to signal to user 711 if his or her exercise result data fall outside a preset acceptable range, allowing the user to self-correct mid-workout.

In addition to being displayed, the exercise result data is stored in exercise result storing and uploading system 723, and then uploaded to a software application after the completion of the exercise or plurality of exercises.

While shown and described herein as a method, system, and device for determining, displaying, storing, and uploading exercise result data, it is understood that the invention further provides various alternative embodiments. For example, in one embodiment, the invention provides a computer-readable/useable medium that includes computer program code to enable a computer infrastructure to determine, display, store, and upload exercise result data. To this extent, the computer-readable/useable medium includes program code that implements each of the various process steps of the invention. It is understood that the terms computer-readable medium or computer useable medium comprises one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory 715 (FIG. 7) and/or storage system 719 (FIG. 7) (e.g., a fixed disk, a read-only memory, a random access memory, a cache memory, etc.), and/or as a data signal (e.g., a propagated signal) traveling over a network (e.g., during a wired/wireless electronic distribution of the program code).

In another embodiment, the invention provides a business method that performs the process steps of the invention on a subscription, advertising, and/or fee basis. That is, a service provider could offer to determine, display, store, and upload exercise result data. In this case, the service provider can create, maintain, support, etc., a computer infrastructure, such as computer infrastructure 712 (FIG. 7) that performs the process steps of the invention for one or more customers. In return, the service provider can receive payment from the customer(s) under a subscription and/or fee agreement and/or the service provider can receive payment from the sale of advertising content to one or more third parties.

In still another embodiment, the invention provides a computer-implemented method for determining, displaying, storing, and uploading exercise result data. In this case, a computer infrastructure, such as computer infrastructure 712 (FIG. 7), can be provided and one or more systems for performing the process steps of the invention can be obtained (e.g., created, purchased, used, modified, etc.) and deployed to the computer infrastructure. To this extent, the deployment of a system can comprise one or more of (1) installing program code on a computing device, such as computer system 713 (FIG. 7), from a computer-readable medium; (2) adding one or more computing devices to the computer infrastructure; and (3) incorporating and/or modifying one or more existing systems of the computer infrastructure to enable the computer infrastructure to perform the process steps of the invention.

As used herein, it is understood that the terms "program code" and "computer program code" are synonymous and mean any expression, in any language, code or notation, of a set of instructions intended to cause a computing device having an information processing capability to perform a particular function either directly or after either or both of the following: (a) conversion to another language, code or notation; and/or (b) reproduction in a different material form. To this extent, program code can be embodied as one or more of: an application/software program, component software/a library of functions, an operating system, a basic I/O system/driver for a particular computing and/or I/O device, and the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method for monitoring and guiding a user through an exercise program, comprising:
providing an automated personal trainer device for monitoring at least one exercise repetition, the automated personal trainer device including a portable monitoring device and a pulley unit, wherein the pulley unit includes
a first pulley wheel,
a second pulley wheel,
a clip springably connecting the first pulley wheel to the second pulley wheel, and
a potentiometer affixed and operably connected to an axle of the first pulley wheel for recording exercise result data;
removably affixing the monitoring unit to a cable-driven workout structure having at least one cable;
removably engaging the clip with a cable of the workout structure, wherein the removably engaging includes pinching the cable between the first pulley wheel and the second pulley wheel;
determining a result of the exercise repetition, the determining including
using the potentiometer to measure a movement of the first pulley wheel as a user completes an exercise, and
measuring a speed and a position of the cable relative to a fixed point;
wherein the result of the exercise repetition includes a speed at which the user is performing the at least one exercise repetition, a range of motion over which the user is performing the at least one exercise repetition, and a resistance against which the user is performing the at least one exercise repetition;
transmitting the result of the exercise repetition to the monitoring unit; and
storing the result in a portable memory device for upload to a personal computer for monitoring and guiding the user through the exercise program, the portable memory device being operably connected to the portable monitoring device.

2. The method of claim 1, further comprising inputting a predetermined requirement for a range of motion at which the at least one exercise repetition is to be performed.

3. The method of claim 2, further comprising providing a signal to the user, based on the result, when the user fails to meet the predetermined requirement for the range of motion in the at least one exercise repetition.

4. The method of claim 2, wherein the range of motion predetermined requirement includes a target extended position value and a target rescinded position value for the at least one exercise repetition.

5. The method of claim 1, wherein the result is displayed to the user in real-time.

6. The method of claim 1, wherein the resistance is one of: mass resistance, hydraulic resistance, and pneumatic resistance.

7. The method of claim 1, further comprising logging onto a web-based site that hosts an on-line community for offering exercise tips, nutritional guidelines, and on-line support.

8. The method of claim 1, further comprising uploading the result to an internet application.

9. The method of claim 1, further including powering the portable monitoring unit with a rechargeable battery.

10. A system for monitoring and guiding a user through an exercise program, comprising:
a pulley unit system for determining a result of at least one exercise repetition,
wherein the pulley unit includes a first pulley wheel, a second pulley wheel, a clip springably connecting the first pulley wheel to the second pulley wheel, and
a potentiometer affixed and operably connected to an axle of the first pulley wheel for recording exercise result data;

wherein the result includes a speed by which the user is performing the exercise repetition, a range of motion over which the user is performing the exercise repetition, and a resistance against which the user is performing the exercise repetition;

a system for storing the result or a plurality of results in a portable memory device the portable memory device being operably connected to a portable monitoring device; and a system for uploading the result or the plurality of results in the portable memory device to a personal computer for monitoring and guiding the user through the exercise program, wherein the portable monitoring device is attached to at least one cable of a cable-driven workout structure, wherein the attaching includes pinching the cable between the first pulley wheel and the second pulley wheel, and wherein the portable monitoring device measures the speed and position of the at least one cable relative to a fixed point.

11. The system of claim 10, wherein a predetermined requirement for the exercise repetition is determined by the user, the predetermined requirement including a range of motion at which the at least one exercise repetition is to be performed.

12. The system of claim 11, wherein a signal is provided to the user, based on the result, when the user fails to meet the predetermined requirement for the range of motion in the exercise repetition.

13. The system of claim 10, wherein the result is displayed to the user in real-time.

14. The system of claim 10, wherein the resistance is one of: mass resistance, hydraulic resistance, and pneumatic resistance.

15. A device for monitoring and guiding a user through an exercise program, the device comprising:
   a pulley unit for collecting exercise result data, the pulley unit including:
      a first pulley wheel,
      a second pulley wheel,
      a clip springably connecting the first pulley wheel to the second pulley wheel,
         wherein the clip further removably secures the pulley unit to a cable of a cable-driven exercise structure, wherein the removably securing includes pinching the cable between the first pulley wheel and the second pulley wheel, and
      a potentiometer affixed and operably connected to an axle of the first pulley wheel for recording exercise result data;
   a portable monitoring unit for displaying and storing the exercise result data; and
   a wire for communicating the exercise result data from the pulley unit to the monitoring unit.

16. The device of claim 15, wherein the portable monitoring unit comprises:
   a memory for storing the exercise result data;
   a display screen for displaying the exercise result data in real time; and
   an input interface for receiving exercise parameter input.

17. The device of claim 16, wherein the memory for storing exercise result data is a memory stick.

18. The device of claim 16, wherein the exercise parameter input includes a range of motion.

19. The device of claim 15, wherein the device is portable.

20. The device of claim 15, wherein the portable monitoring unit further comprises at least one magnet affixed to the monitoring unit for removably securing the device to the exercise structure.

* * * * *